(12) United States Patent
Toon et al.

(10) Patent No.: US 11,331,124 B2
(45) Date of Patent: *May 17, 2022

(54) MODULAR TULIP ASSEMBLY

(71) Applicant: Spinal Elements, Inc., Carlsbad, CA (US)

(72) Inventors: Geoffrey Toon, Vista, CA (US); David Cain, Marietta, GA (US); Joshua Gunn, Marietta, GA (US)

(73) Assignee: Spiral Elements, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/663,175

(22) Filed: Oct. 24, 2019

(65) Prior Publication Data

US 2020/0054376 A1 Feb. 20, 2020

Related U.S. Application Data

(63) Continuation of application No. 15/284,929, filed on Oct. 4, 2016, now Pat. No. 10,485,594.

(51) Int. Cl.
*A61B 17/70* (2006.01)
*A61B 17/86* (2006.01)

(52) U.S. Cl.
CPC ...... *A61B 17/7037* (2013.01); *A61B 17/7035* (2013.01); *A61B 17/863* (2013.01); *A61B 17/8605* (2013.01)

(58) Field of Classification Search
CPC .............. A61B 17/7037; A61B 17/7035
See application file for complete search history.

(56) References Cited

U.S. PATENT DOCUMENTS

| 5,549,608 | A | 8/1996 | Errico et al. |
|---|---|---|---|
| 5,733,285 | A | 3/1998 | Errico et al. |
| 5,964,760 | A | 10/1999 | Richelsoph |
| 7,087,057 | B2 | 8/2006 | Konieczynski et al. |
| 7,942,911 | B2 | 5/2011 | Doubler et al. |
| 8,241,341 | B2 | 8/2012 | Walker et al. |
| 8,377,101 | B2 | 2/2013 | Barrus et al. |
| 8,465,530 | B2 | 6/2013 | Hammill et al. |
| 9,055,983 | B1 | 6/2015 | Radcliffe et al. |
| 9,155,568 | B2 | 10/2015 | Biedermann et al. |

(Continued)

OTHER PUBLICATIONS

Official Communication (International Preliminary Report on Patentability) (DN0302PCT) dated Apr. 18, 2019 with Written Opinion dated Nov. 8, 2017.

(Continued)

*Primary Examiner* — Andrew Yang

(57) ABSTRACT

A modular tulip assembly has a rod receiving tulip and a saddle. The saddle is interlockingly held inside a distal portion of the tulip. The saddle has an external locking groove or recess. The tulip has a locking projection. The locking projection is positioned into the external locking groove or recess and holds the saddle in a pre-loaded unlocked state ready to be pushed onto a head of an implanted bone screw. Upon receiving the head of the bone screw, the saddle can be moved distally relative to the tulip to a locked state by moving the locking groove or recess distally past the locking projection to where the proximal end of the saddle is past abutting the locking projection.

19 Claims, 16 Drawing Sheets

(56) References Cited

U.S. PATENT DOCUMENTS

| | | |
|---|---|---|
| 9,155,579 B2 | 10/2015 | Konieczynski et al. |
| 9,186,187 B2 | 11/2015 | Mishra |
| 9,198,694 B2 * | 12/2015 | Mishra ............... A61B 17/7032 |
| 2010/0114170 A1 | 5/2010 | Barrus et al. |
| 2010/0152787 A1 | 6/2010 | Walsh |
| 2010/0160978 A1 | 6/2010 | Carbone |
| 2010/0234902 A1 | 9/2010 | Biedermann |
| 2012/0277806 A1 | 11/2012 | Smith |
| 2014/0163619 A1 * | 6/2014 | Harvey .............. A61B 17/7037 606/278 |
| 2014/0188175 A1 | 7/2014 | Mishra et al. |
| 2015/0230829 A1 | 8/2015 | Harris et al. |
| 2016/0000471 A1 | 1/2016 | Konieczynski et al. |
| 2016/0066959 A1 | 3/2016 | Biedermann et al. |
| 2016/0206357 A1 | 7/2016 | Whipple et al. |
| 2016/0361096 A1 | 12/2016 | van Der Pol |

OTHER PUBLICATIONS

Official Communication (International Search Report) (DN0302PCT) dated Nov. 8, 2017.

* cited by examiner

MODULAR TULIP ASSEMBLY

CROSS-REFERENCE TO RELATED APPLICATIONS

This application is a continuation of U.S. patent application Ser. No. 15/284,929 filed Oct. 4, 2016 titled A MODULAR TULIP ASSEMBLY, which is incorporated by reference herein.

TECHNICAL FIELD

The present invention relates to an improved modular head tulip assembly.

BACKGROUND OF THE INVENTION

Bone anchor screws come in a variety of shapes and sizes. One of the more common styles has a polyaxial head that allows for the screw to enter the bone structure at an ideal or preferred inclination. To achieve this polyaxial inclination, the head has a shape configured to allow a complimentary implant device being held by the screw to rotate about its lower external surface. This lower surface can be one of a number of shapes like conical or spherical or hemispherical. This ability is often used in rod receiving implant devices having a modular head assembly.

The modular head pedicle screw assembly generally includes a tulip. A tulip is a body structure having two opposing sides spaced by a slotted opening to receive a spinal rod. The tulip often employs internal threads to receive a rod locking set screw to anchor or fix the rod in the tulip. The lower portion of the tulip has an opening to receive the pedicle screw in a base seat. Often, the tulip can have a saddle that also supports the rod along an underside of the rod. The saddle having an upper recessed curvature into which the rod sits and a lower cup like opening to receive the top of the pedicle screw head. When the saddle and rod and set screw are tightened, the screw angle is fixed against the tulip seat.

Often, it is preferred that the pedicle screw is first placed securely in the bone structure leaving the head protruding above the bone surface. In this surgical procedure the tulip assembly must be adapted to fit down onto the projecting screw head. To accomplish this, the surgeon must push the tulip onto and over the screw head without a clear path of vision. Accordingly, the placement must be accomplished without any way of knowing if the tulip or other device is properly secured. Thereafter, the device is tightened to complete the assembly and the only way to insure the assembly is secure requires an upward pulling of the tightened assembly. This is not a good test because the assembly may be loosened or the screw to bone interface weakened.

It is, therefore, an objective of the present invention to provide a way for a surgeon to place a tulip assembly onto a pedicle screw already threaded into bone in such a way the surgeon can make a proper and secure connection easily.

It is a further objective that the device has properly fitted the tulip assembly onto the pedicle screw head by the very nature of the design. It is another objective that the device provides a self-locking feature that when tightened by assembly, the surgeon can lock the assembly engagement insuring he has made a proper assembly. These and other objectives are achieved by the invention as described hereinafter.

SUMMARY OF THE INVENTION

A modular tulip assembly has a rod receiving tulip and a saddle. The saddle is interlockingly held inside a distal portion of the tulip. The saddle has an external locking groove or recess. The tulip has a locking projection. The locking projection is positioned into the external locking groove or recess and holds the saddle in a pre-loaded unlocked state ready to be pushed onto a head of an implanted bone screw. Upon receiving the head of the bone screw, the saddle can be moved distally relative to the tulip to a locked state by moving the locking groove or recess distally past the locking projection to where the proximal end of the saddle is past abutting the locking projection.

The tulip has a pair of opposing internally threaded walls defining a slotted opening for receiving a rod, an open bore with an open distal end for passing the polyaxial head of the bone screw, and the locking projection is axially spaced below the internal threads of the opposing walls and above the open distal end.

The saddle has an axis defined by a center opening. The saddle has a proximal end with a concavity for holding a rod and a distal portion with a plurality of arcuate fingers spaced by slots. The plurality of arcuate fingers are curved to form at least a hemispherical shaped concavity for receiving and holding the head of the bone screw. The fingers extend to a distal end. The saddle has the exterior locking groove or recess positioned between the proximal end and above the arcuate fingers. The saddle is sized to pass through the open distal end of the tulip and move axially inside the tulip below the internal threads. The tulip has an enlarged internal chamber to accommodate the arcuate fingers and sized to allow the fingers to flex outwardly over and past a maximum diameter of the screw head on attachment.

In one embodiment, the saddle center opening at the proximal end has internal threads to engage threads of an end of a tool configured to axially move the saddle relative to the tulip. The saddle is pre-positioned in an unlocked bone screw receiving state when the locking groove or recess is moved onto the locking projection and after being attached onto an implanted bone screw polyaxial hemispherical head, the saddle is configured to be moved relative to the tulip by rotation of the tool to the locked state by moving the locking groove or recess distally off the locking projection and having the proximal end of the saddle moved distally past and abutting the locking projection causing the arcuate fingers at the distal end to flex and be compressed at the open distal end of the tulip. The locked saddle can be repositioned to the unlocked state by attaching the threaded end of the tool to the saddle and rotating the tool as it abuts a proximal end of the tulip causing the saddle locking groove or recess to engage the locking projection and move onto the locking projection allowing the arcuate fingers to release the screw head and the tulip assembly to be removed from the bone screw.

In a preferred embodiment, a modular tulip assembly is configured to receive and lock onto an implanted bone screw having a threaded shank and a hemispherical polyaxial head. The tulip subassembly has a tulip and a saddle. The tulip has a pair of opposing internally threaded walls defining a slotted opening for receiving a rod, an open bore with an open distal end for passing the polyaxial head of the bone screw, and a locking projection being axially spaced below the internal threads of the opposing wall and above the open distal end. The saddle has an axis defined by a center opening. The saddle has a proximal end with a concavity for holding the rod and a distal portion with a plurality of arcuate fingers spaced by slots. The plurality of fingers are curved to form at least a hemispherical shaped concavity for receiving and holding the head of the bone screw. The fingers extend to a distal end, the saddle has an exterior locking groove or recess positioned between the proximal end and above the arcuate fingers. The saddle is sized to pass through the open distal end and move axially inside the tulip below the internal threads. When assembled to the tulip, the saddle is pre-positioned in an unlocked bone screw receiving state when the locking groove or recess is moved onto the locking projection. Thereafter, the saddle in the unlocked state can be attached onto an implanted bone screw polyaxial hemispherical head. The saddle is configured to be moved to a second locked state by moving the locking groove or recess distally off the locking projection and having the proximal end of the saddle moved distally past and abutting the locking projection causing the arcuate fingers at the distal end of the tulip to flex and be compressed at the open distal end of the tulip.

In this preferred embodiment, the tulip has an enlarged internal chamber to accommodate the arcuate fingers and sized to allow the fingers to flex outwardly over and past a maximum diameter of the screw head on attachment. The saddle center opening at the proximal end has internal threads to engage threads of an end of a tool configured to axially move the saddle relative to the tulip. The modular tulip assembly has the saddle pre-positioned in an unlocked bone screw receiving state when the locking groove or recess is moved onto the locking projection and after being attached onto an implanted bone screw polyaxial hemispherical head, the saddle is configured to be moved relative to the tulip by rotation of the tool to the locked state by moving the locking groove or recess distally off the locking projection and having the proximal end of the saddle moved distally past and abutting the locking projection causing the arcuate fingers at the distal end to flex and be compressed at the distal end of the tulip. The modular tulip assembly allows the locked saddle to be repositioned to the unlocked state by attaching the threaded end of the tool to the saddle and rotating the tool as it abuts a proximal end of the tulip causing the saddle locking groove or recess to reengage the locking projection and move onto the locking projection allowing the arcuate fingers to release the screw head allowing the tulip assembly to be removed from the bone screw.

A method of assembling a modular tulip has the step of providing a tulip with a distal and a proximal projection; and positioning a saddle with a concave locking surface inside the tulip over and past the distal projection and onto the proximal projection inside the tulip in a pre-loaded unlocked state to receive a head of a bone screw. The method further has the step of pushing the tulip with the pre-loaded unlocked saddle onto an implanted bone screw previously threaded into bone and moving the saddle to a locked state by moving the locking groove or recess distally off the locking projection and the proximal end distally abuts the locking projection. The step of moving the saddle to a locked position further includes engaging internal threads of the saddle with a threaded end of a tool, rotating the tool to move the saddle from the pre-loaded unlocked state to the locked state after attaching the implanted screw. The method further has the step of unlocking the locked tulip assembly by moving the saddle by moving the saddle from the locked state to the pre-loaded unlocked state. The step of unlocking is accomplished by engaging threads of the saddle with the threaded end of the tool and rotationally pulling the saddle proximally relative to the tulip.

BRIEF DESCRIPTION OF THE DRAWINGS

The invention will be described by way of example and with reference to the accompanying drawings in which.

DETAILED DESCRIPTION OF THE INVENTION

Figure 1:
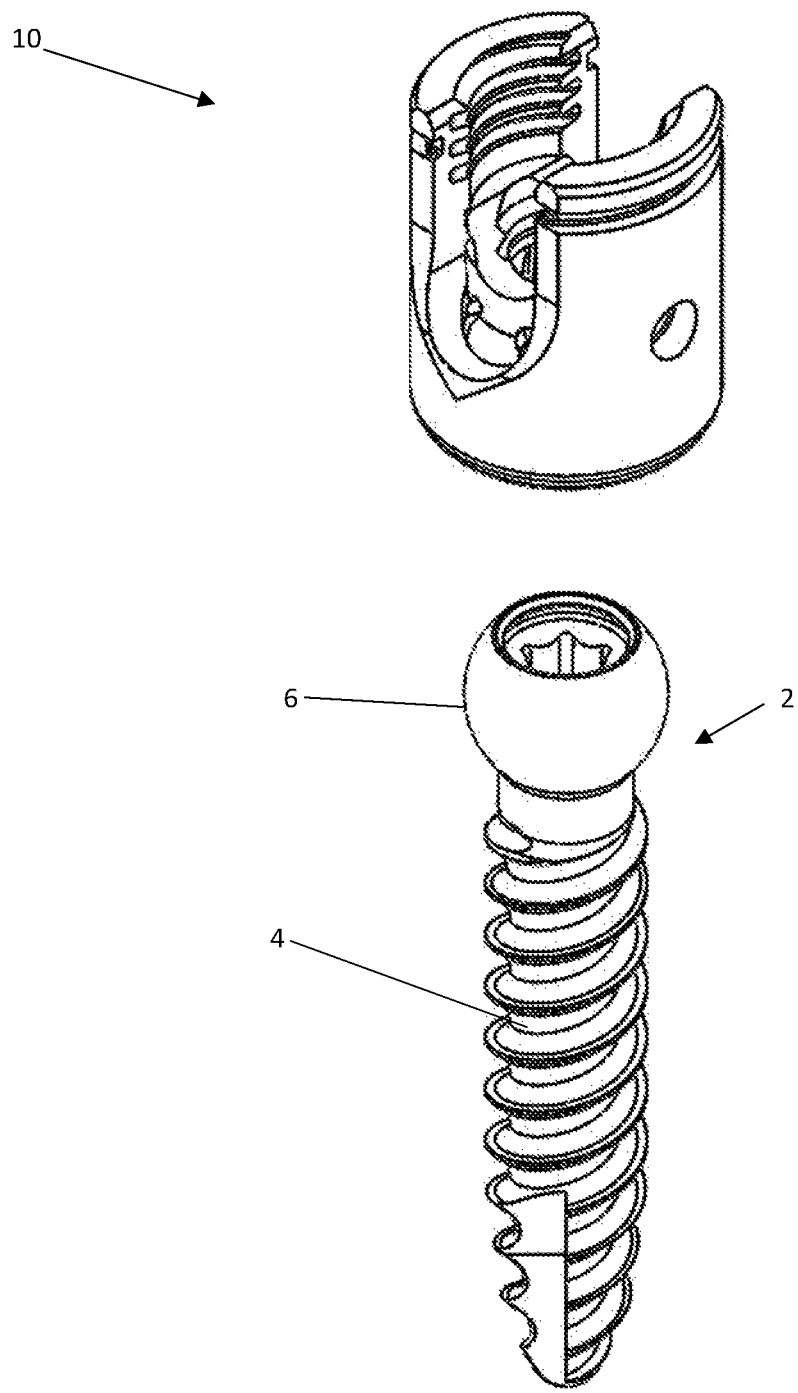
FIG. 1 is a perspective view of the tulip assembly positioned above an exemplary bone screw.

With reference to FIG. 1, a perspective view of the modular tulip assembly 10 of the present invention is shown. As shown, the modular tulip assembly 10 has a rod receiving tulip 20, and internal of the rod receiving tulip 20 is shown a saddle 40, the saddle 40 is interlockingly held inside a distal portion of the tulip 20. Below the tulip assembly 10, is shown an exemplary bone screw 2. The bone screw 2 has a threaded shank 4 for engaging bone and a rounded spherical or hemispherical head 6 at the proximal end of the shank 4. This head 6 is configured to provide polyaxial movement of the bone screw 2 relative to the tulip assembly 10 on assembly. This polyaxial movement is maintained as long as the tulip assembly 10 is not locked into position and fixed.

The modular tulip assembly 10 is basically a two part device with the tulip 20 and the preloaded saddle 40 for use with a bone screw 2. The bone screw 2 can be preloaded into the assembly 10 to make a three component device or system if desired. An important feature of the present invention is a binary locking aspect where a single locking projection 25 in combination with a recess or groove 42 holds the saddle 40 in a preloaded state inside the modular tulip 20 and when the modular tulip assembly 10 is moved onto the head 6 of a bone screw 2 the saddle 40 can be moved into a locked state and, if desired, can be unlocked in a reversible fashion making the modular tulip assembly 10 most convenient to use. These features are fully described in detail as follows.

Figure 2:
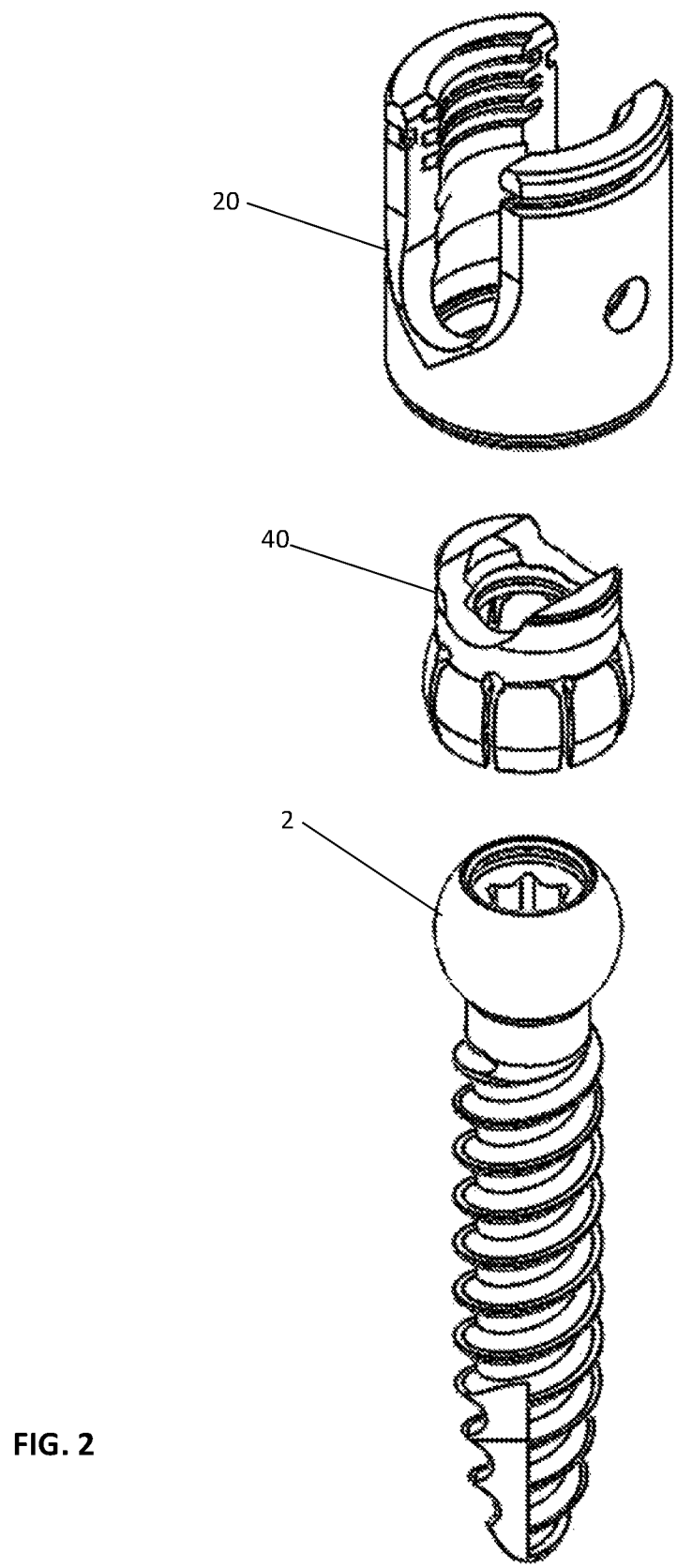
FIG. 2 is an explode perspective view of the tulip and saddle of the present invention above an exemplary bone screw.

With reference to FIG. 2, the modular tulip assembly 10 is shown in an exploded view with the saddle 40 shown below and between the tulip 20 and the bone screw 2.

Figure 3:
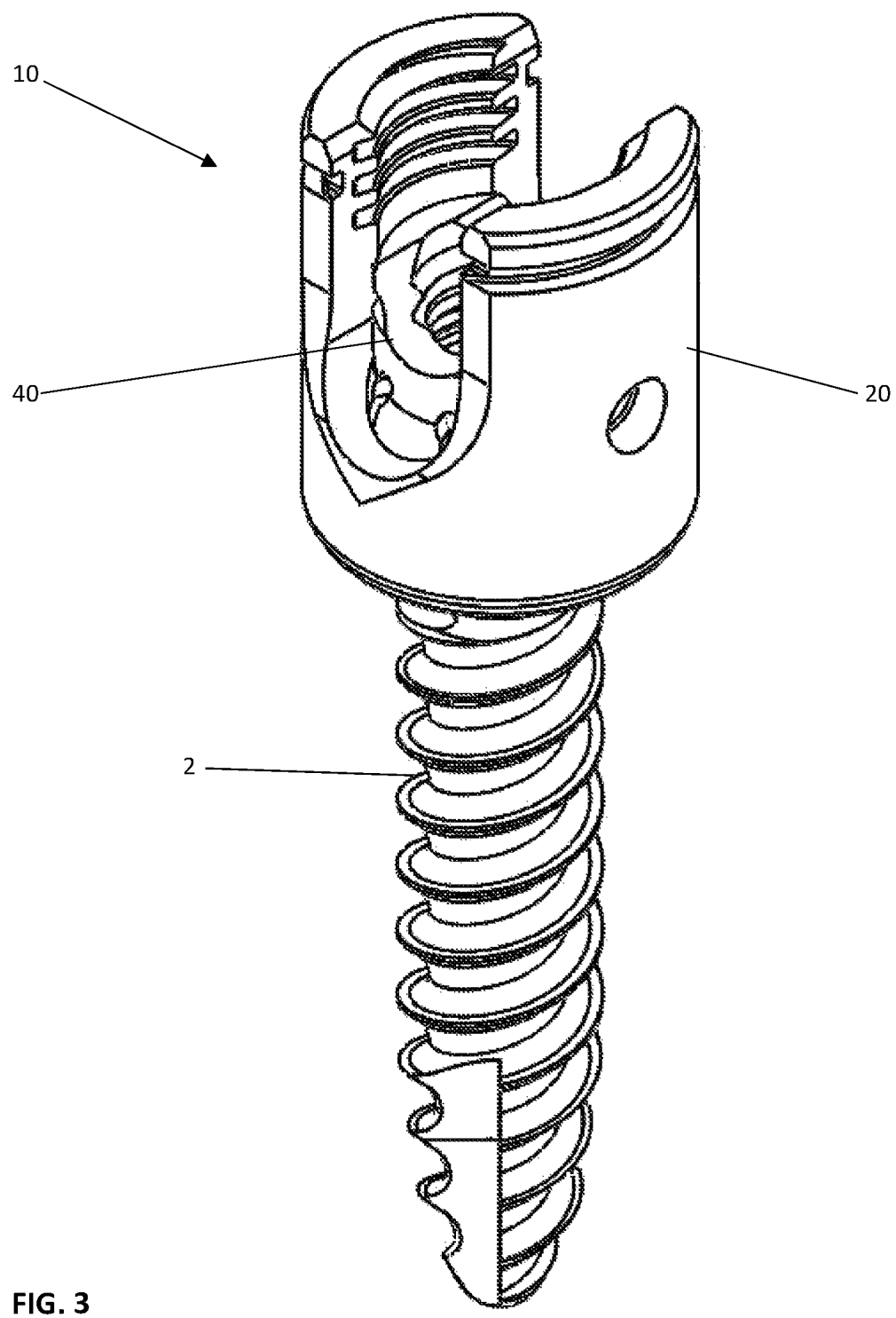
FIG. 3 is a perspective view of the tulip assembly shown attached to the exemplary bone screw.
Figure 13:
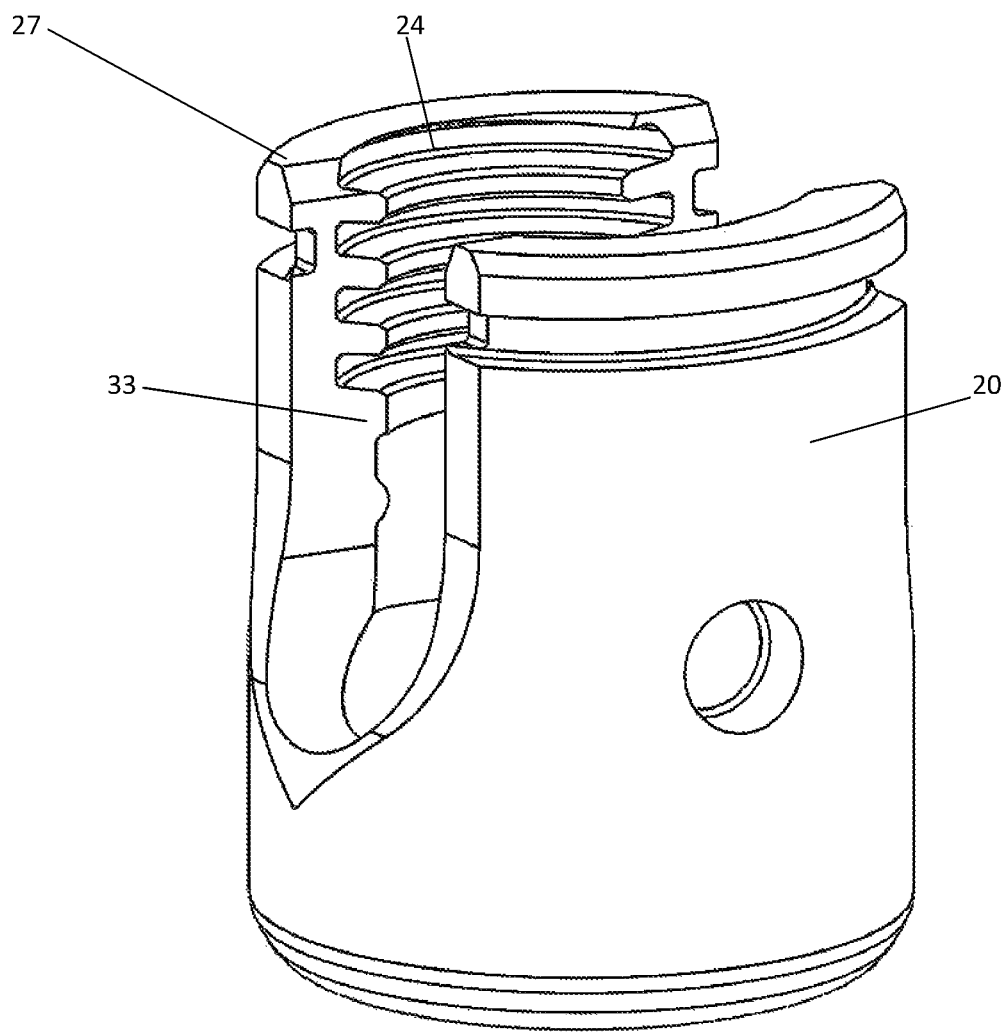
FIG. 13 is a perspective view of the tulip of the present invention.
Figure 14:
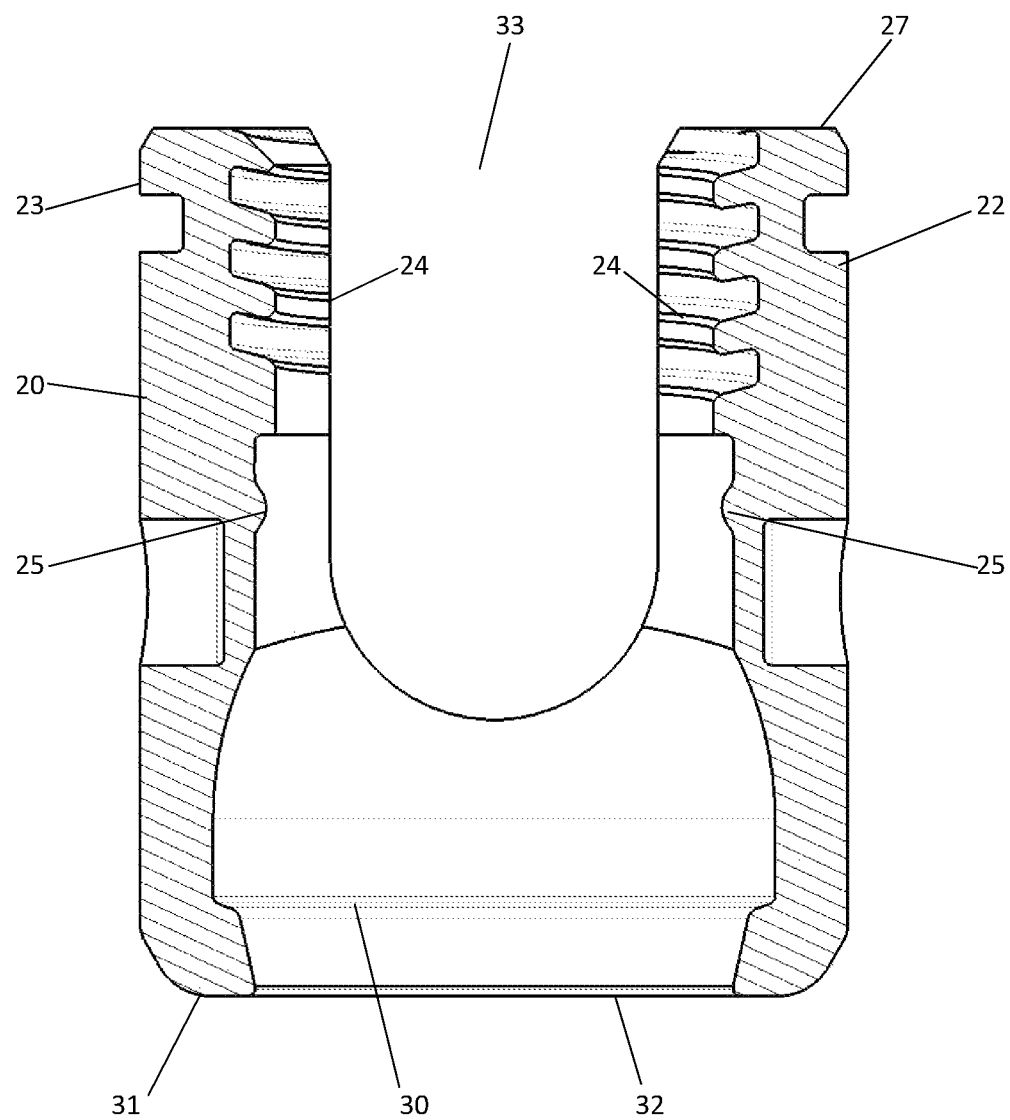
FIG. 14 is a cross-sectional plan view of the tulip taken from FIG. 13.

In FIG. 3, the tulip assembly 10 is shown attached to the exemplary bone screw 2 in a perspective view. The tulip 20 is fully separately illustrated in FIGS. 13 and 14.

Figure 4:
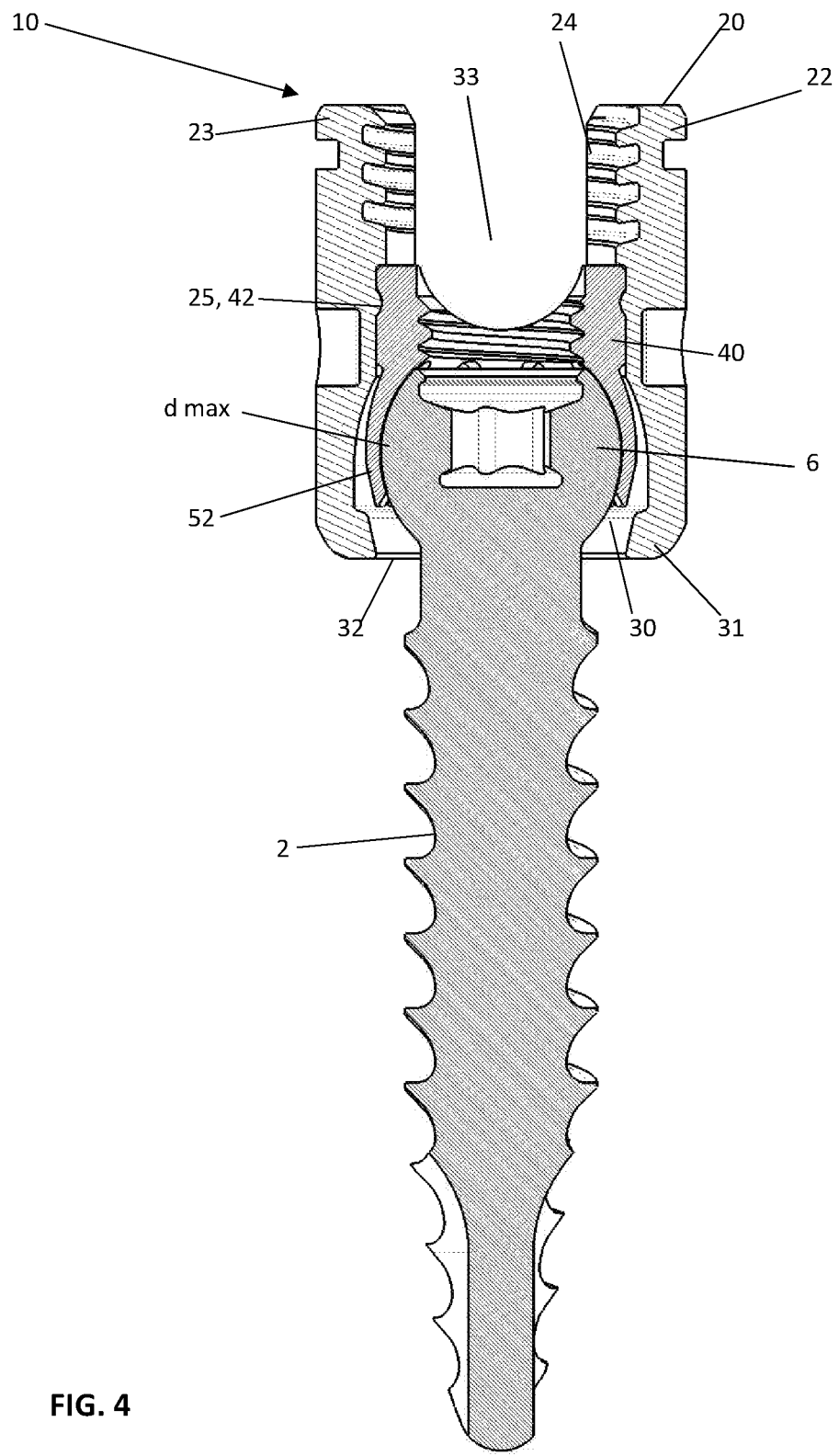
FIG. 4 is a cross-sectional view of the tulip assembly in a pre-loaded unlocked state with the saddle shown attached onto the head of an exemplary bone screw.
Figure 15:
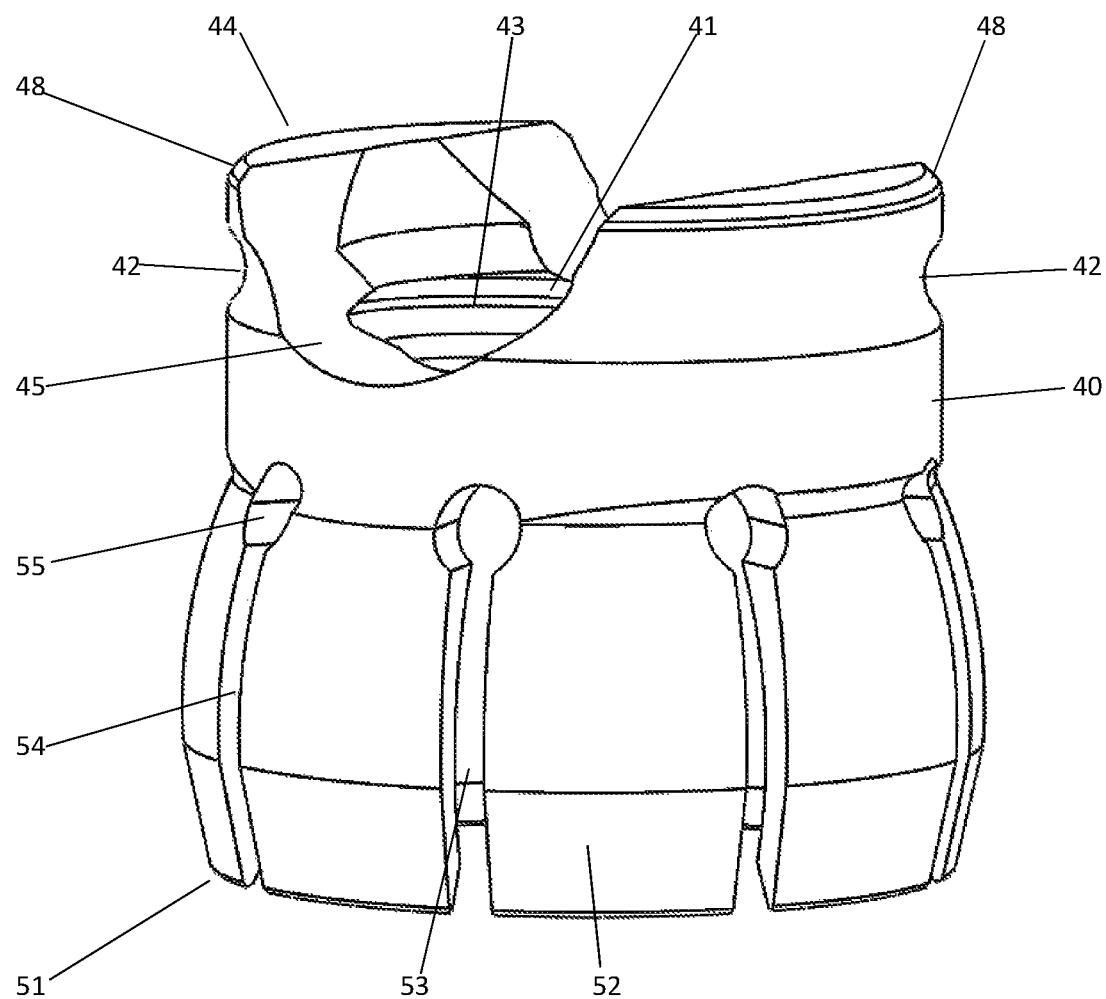
FIG. 15 is a perspective view of the saddle of the present invention.
Figure 16:
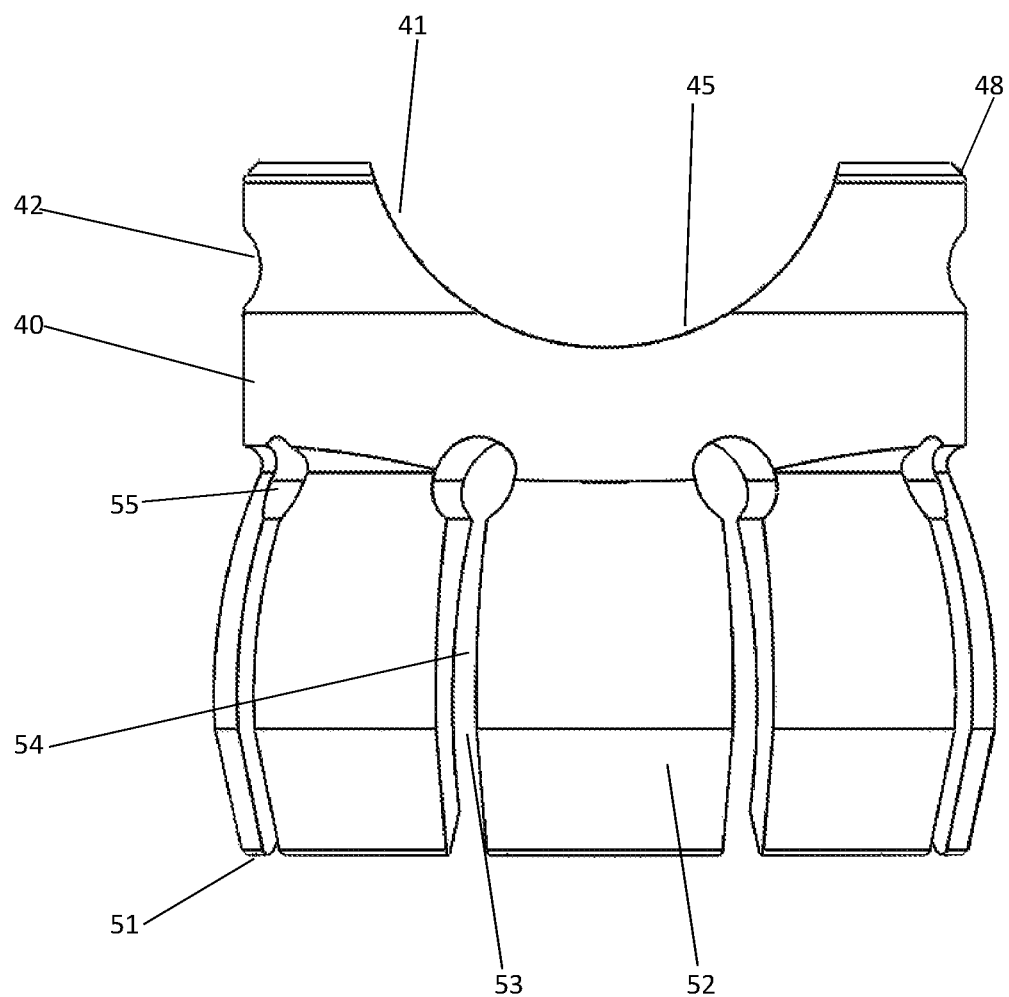
FIG. 16 is a plan view of the saddle taken from FIG. 15.

With reference to FIG. 4, a cross-sectional view of the tulip assembly 10 is shown wherein the saddle 40 is positioned over the polyaxial hemispherical head 6 of the exemplary bone screw 2. As shown in cross-section, the tulip 20 is shown with opposing walls 22, 23 with internal threads 24 defining a rod receiving slot or channel 33. Below the internal threads 24 is illustrated the saddle 40. The saddle has a locking groove or recess 42 affixed to a locking projection 25 in the tulip 20 of the tulip assembly 10. As further shown, and with reference to FIGS. 15 and 16, the saddle 40 has a proximal end 44 with a rod receiving concavity 45 that is aligned with the channel 33 of the tulip 20. At the proximal end 44 of the saddle 40 there is a central opening 41 that is threaded with threads 43, as illustrated. The locking groove or recess 42 is shown near the proximal end 44 of the saddle 40. Below the locking groove or recess 42 is shown a plurality of axially extending flexible fingers 52 that are spaced apart by slots or slits 54. At a distal end 51, these arcuate curved flexible fingers 52 are bowed slightly inwardly. At the proximal end of the slot 54 is an enlarged circular hole 55 to provide stress relief and also increase the flexibility of the fingers 52. This is important in that the fingers 52 must flex or bow outwardly in order to expand as they slide over the hemispherical head 6 of the exemplary bone screw 2. As shown in FIG. 4, the plurality of arcuate fingers 52 extend downward past the maximum diameter (d max) of the polyaxial hemispherical bone screw head 6. The fingers 52 extension creates at least a hemispherical concavity 53 that extends beyond the maximum diameter d max and as such, the curvature of the fingers 52 bends outwardly at the proximal end and bows inwardly towards the distal end 51, however, when attached to the bone screw 2, all of the fingers 52 are shown deflected outwardly. As shown in FIG. 4 and also in FIG. 14, in cross-section, the tulip 20 has a large internal chamber 30 above the distal end 31. This chamber 30 is configured to allow the fingers 52 of the saddle 40 to bow outwardly on assembly. Once the fingers 52 have bowed or flexed outwardly to pass the maximum diameter d max of the bone screw head 6, they will conform or flex back inwardly compressing and sliding against the surface 8 of the hemispherical bone screw head 6. Preferably, the concavity 53 formed by the plurality of arcuate fingers 52 is sized to complimentarily fit the head 6 of the bone screw 2 to which it is to be attached.

Figure 5:
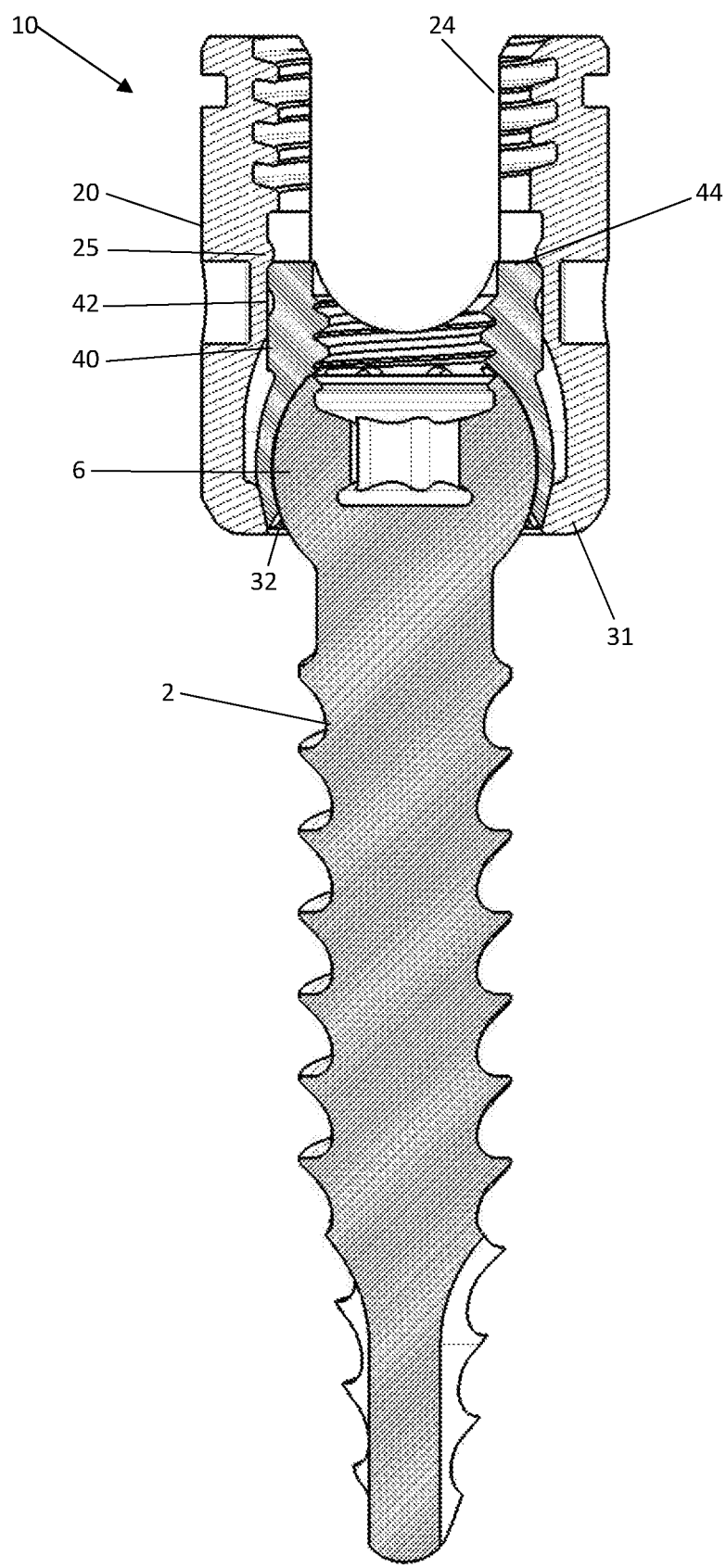
FIG. 5 is a cross-sectional view showing the tulip assembly wherein an internal saddle has been moved to the locked position or state.
Figure 6:
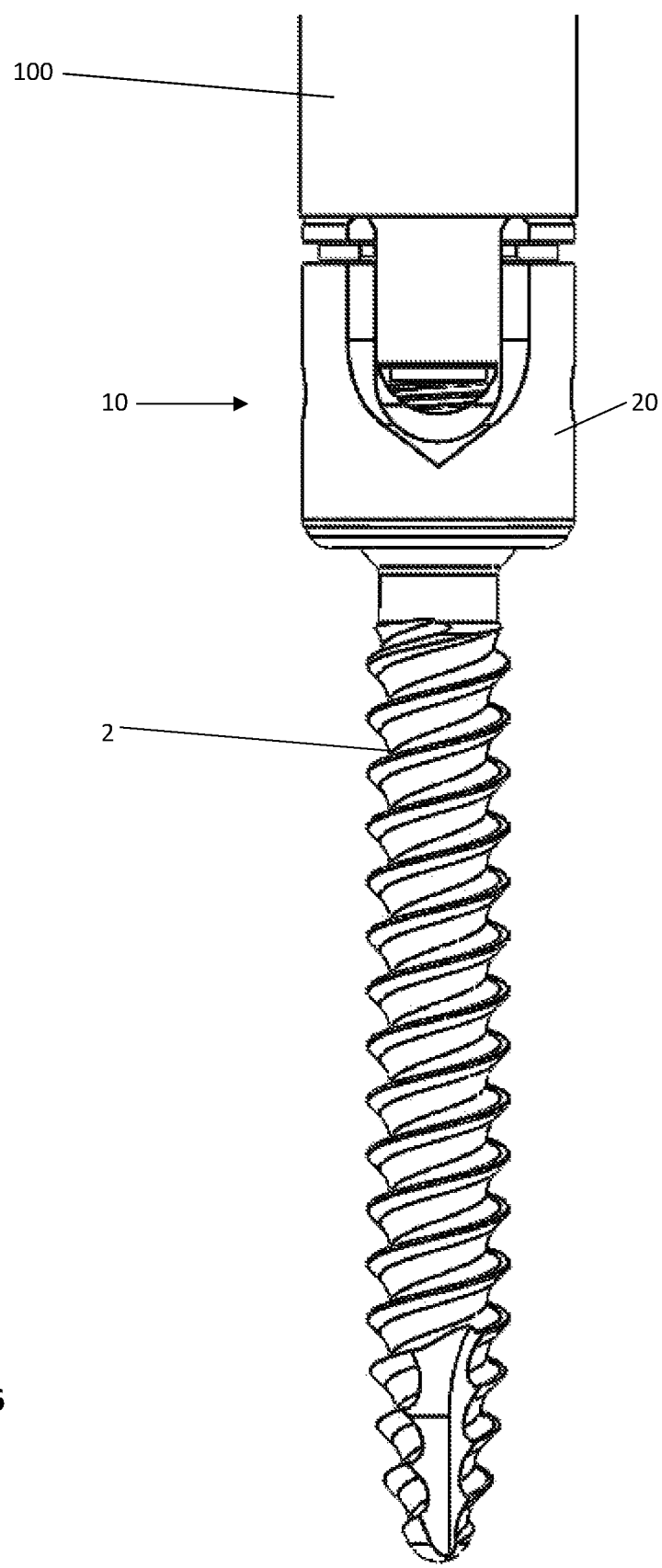
FIG. 6 is a plan view of a tool end with a threaded end for attaching to internal threads of the saddle.

With reference to the proximal end 44 of the saddle 40, as shown, the proximal end 44 is shown above where the grove or recess 42 is positioned over a projection 25 in the tulip 20. The outer or exterior surface of the proximal end 44 has a small rounded edge or chamfer 48 to facilitate sliding over the projection 25. When the saddle 40 is oriented in this position, it is in a preloaded and unlocked position wherein the arcuate extended fingers 52 are allowed to move inwardly and outwardly relative to an axis of the tulip 20. with reference to FIG. 5, the saddle 40 is shown moved in a locking position wherein the proximal end 44 of the saddle 40 is moved past the locking projection 25 of the tulip 20 and the groove or recess 42 is moved from the locking projection 25 and the proximal end 44 of the saddle 40 is move past abutting the locking projection 25. In this state, the saddle 40 is prevented from any proximal movement relative to the tulip 20 and the arcuate fingers 52 have been pressed into the distal opening 32 of the tulip 20 between the head 6 of the polyaxial screw 2 and the distal end 31 of the tulip 20. This causes the arcuate fingers 52 to be flexed inwardly, tightly grasping against the polyaxial head 6 of the bone screw 2. This assembly can be accomplished when the bone screw 2 is implanted in bone. In such a case, the modular tulip assembly 10 with the saddle 40 in the unlocked position can be positioned over the head 6 of the bone screw 2, pushed onto the bone screw 2 and thereafter the saddle 40 moved into the locking position.

Figure 7:
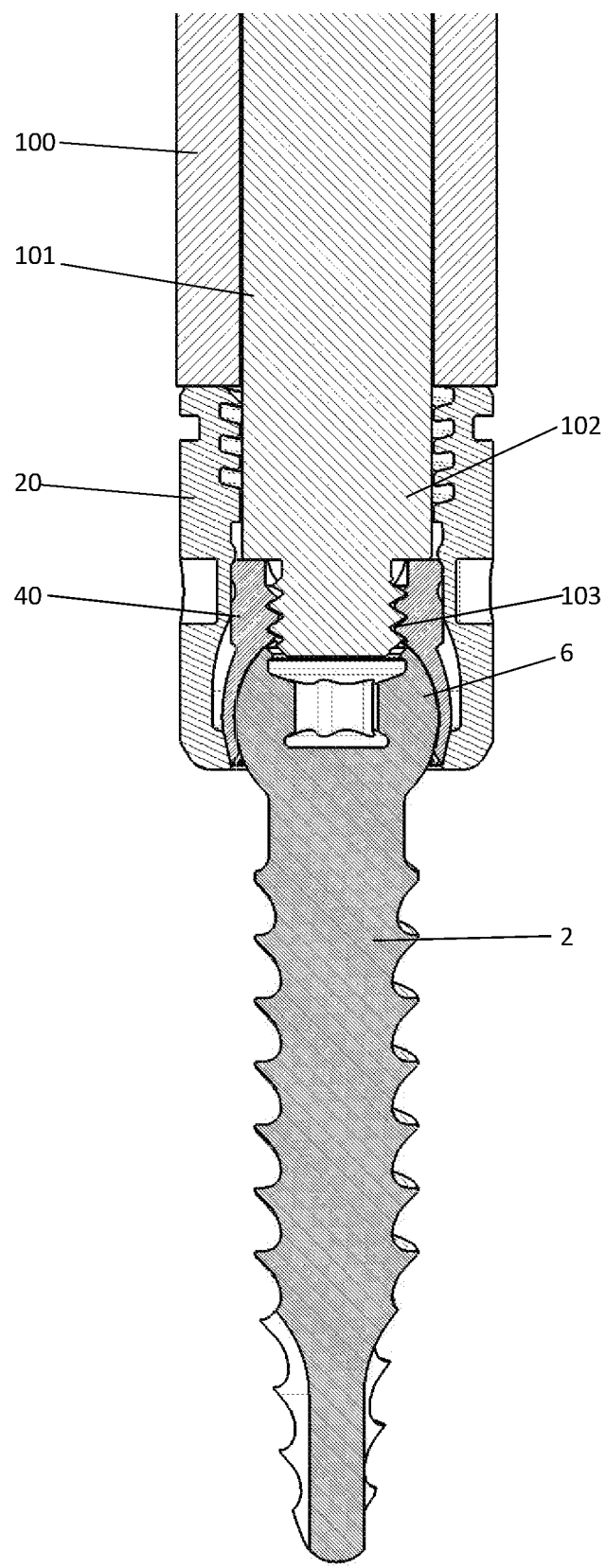
FIG. 7 is a cross-sectional view taken from FIG. 6 showing the tool end threaded into the saddle with the saddle having been moved relative to the tulip into the locked state.
Figure 8:
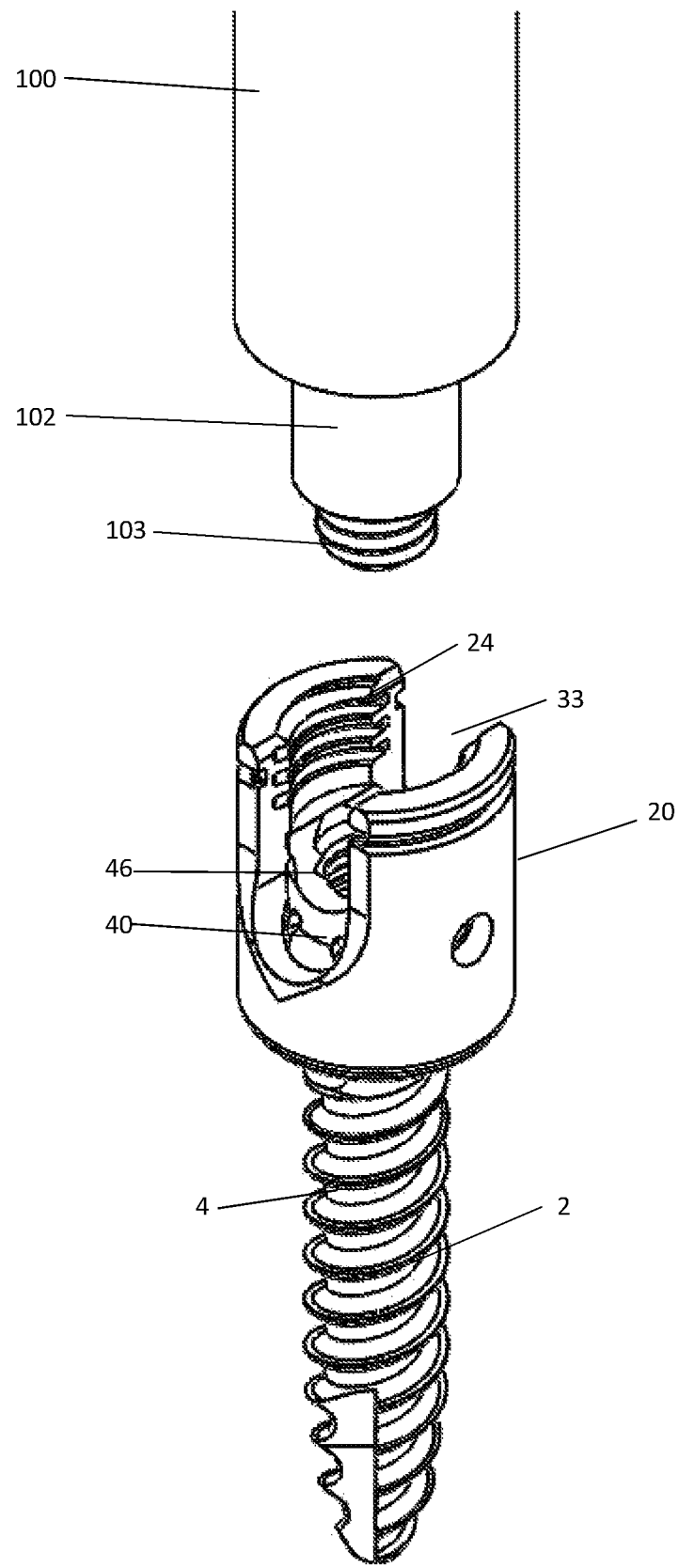
FIG. 8 is a perspective view of the tool end above the tulip assembly and bone screw illustrating removal of the tool after locking or alternatively showing how the tool can be used to unlock the saddle to allow the tulip assembly to be removed from an implanted bone screw.
Figure 9:
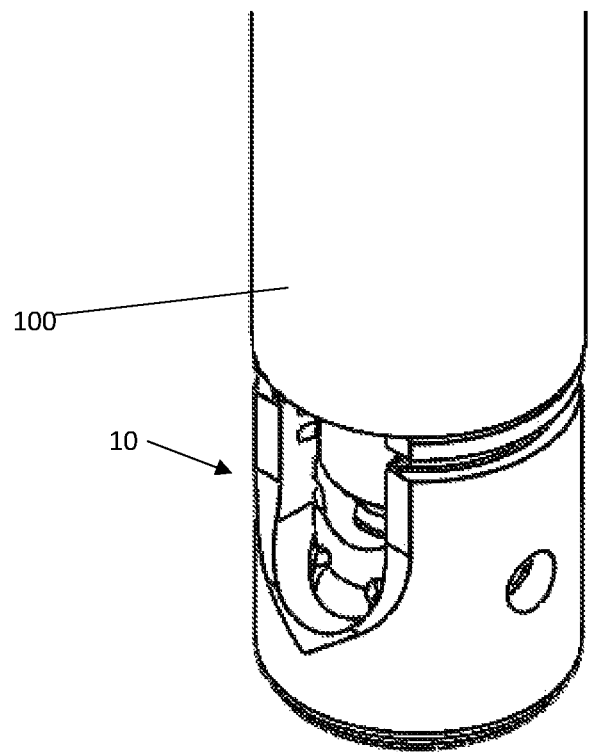
FIG. 9 shows the tulip assembly attached to the tool for either attachment to the exemplary bone screw or alternatively after removal from the bone screw.
Figure 9:
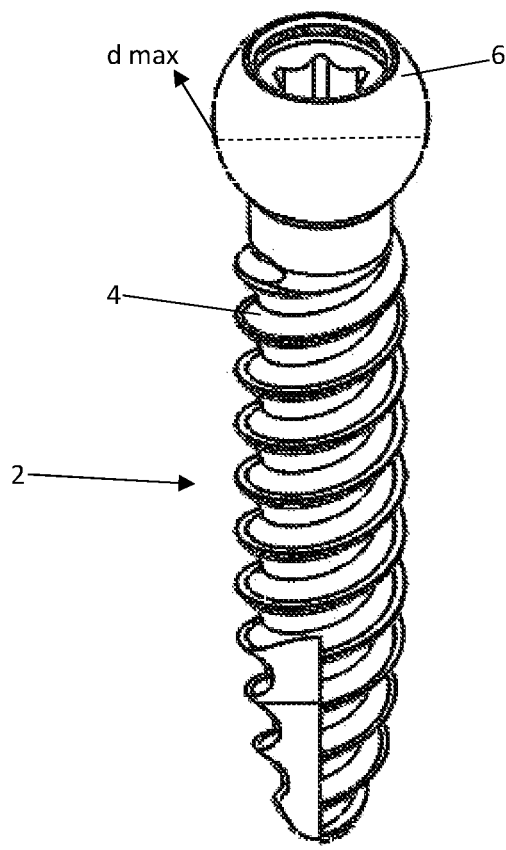
Figure 10:
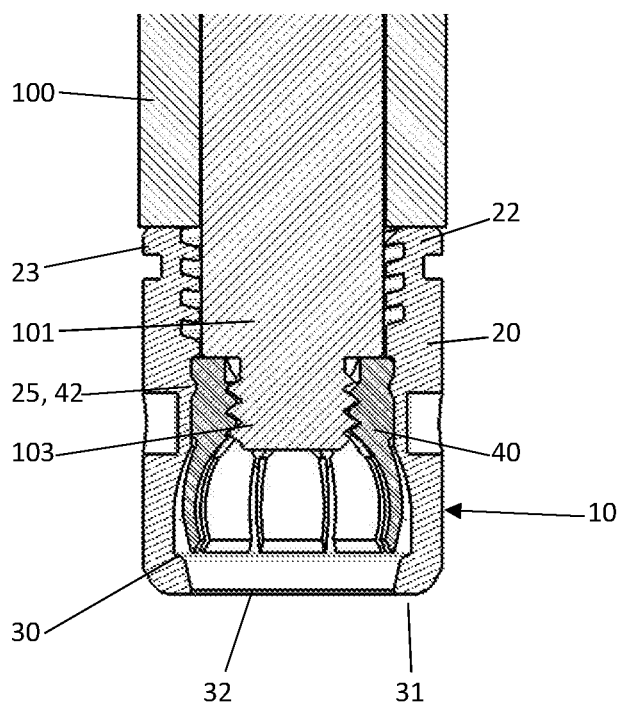
FIG. 10 shows in cross-section the tulip assembly and unlocked saddle attached to the tool for attachment to or alternatively as occurs on removal from said bone screw.
Figure 10:
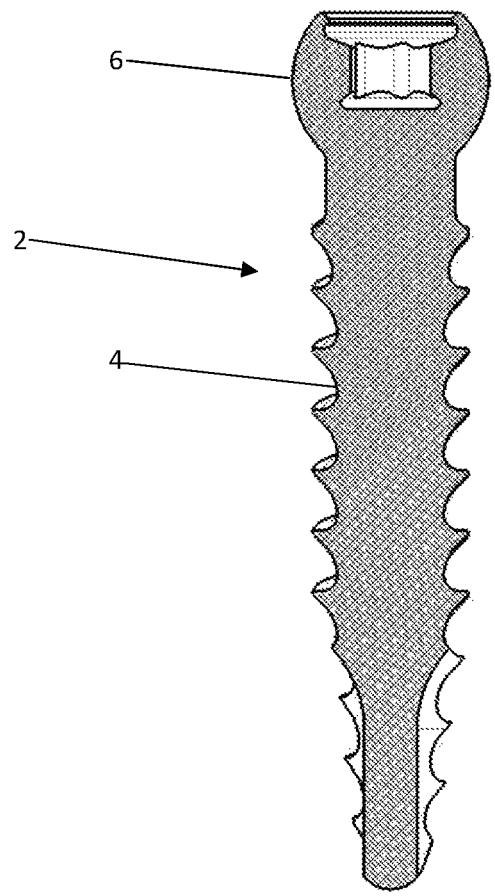

With reference to FIGS. 6-10, the tulip assembly 10 is shown attached to the bone screw 2 with the assistance of a tool 100. The tip 102 of the tool 100, illustrated in FIG. 6, has a threaded end 103, also illustrated in FIG. 7 in a cross-sectional view, that is engaged with the internal threads 43 of the saddle 40. The end 102 of this tool 100 is configured to threadingly engage the saddle 40 and in so doing enables the tool 100 to push against the saddle 40, the outer shoulder 106 of the tool 100 is adapted and precisely dimensioned to abut a proximal end 27 of the tulip 20 along the opposing walls 22, 23. When this occurs and the internal shaft 101 of the tool 100 is rotated, it will push the saddle 40 directly axially distally moving the saddle 40 from the preloaded unlocked position to the locked position as illustrated in FIG. 7. FIG. 8 shows the tool 100 separated from the tulip assembly 10 as the tool 100 is being removed after the assembly is accomplished or FIG. 8 can be viewed alternatively as a removal tool 100 assisted illustration wherein the tulip assembly 10 when attached and locked onto an implanted bone screw 2 can be physically removed by threading the end 103 of the tool 100 into the internal threads 43 of the saddle 40 and rotating in such a fashion that is pulls the saddle 40 in the proximal direction relative to the tulip 20. When this occurs, the saddle 40 will move from the locked position as the fingers 52 will be released from the distal end 51 and moved upward into the chamber 30 within the tulip 20 as the recess or groove 42 is positioned onto the locking projection 25, when this occurs, the tool 100 can be used to pull the tulip 20 with unlocked saddle 40 away from the implanted bone screw 2, as illustrated in FIG. 9. It is understood while the bone screw is shown not embedded in bone just for simplification, it is to be appreciated that this procedure can be accomplished while the bone screw 2 is implanted in a vertebral body. The cross-sectional view of FIG. 10 illustrates how the fingers 52 are allowed to flex when the bone screw 2 has been removed and a saddle 40 is prepositioned in the unlocked state.

Figure 11:
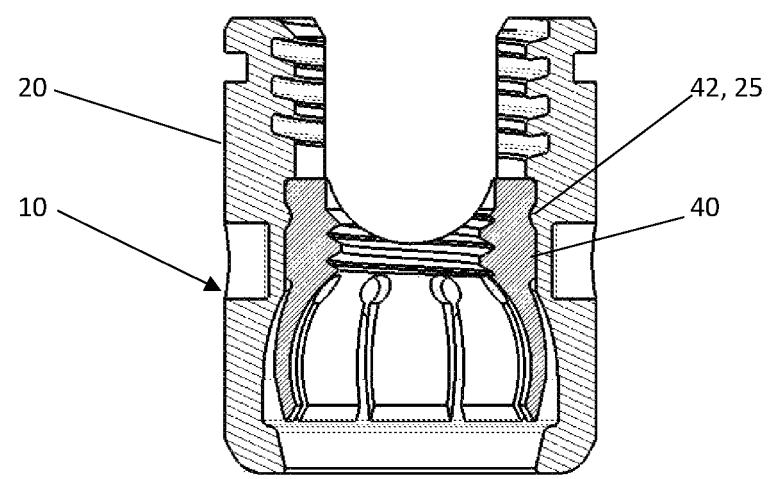
FIG. 11 is a cross-sectional view illustrating the tulip assembly with the saddle in a preloaded unlocked state over an exemplary bone screw.
Figure 11:
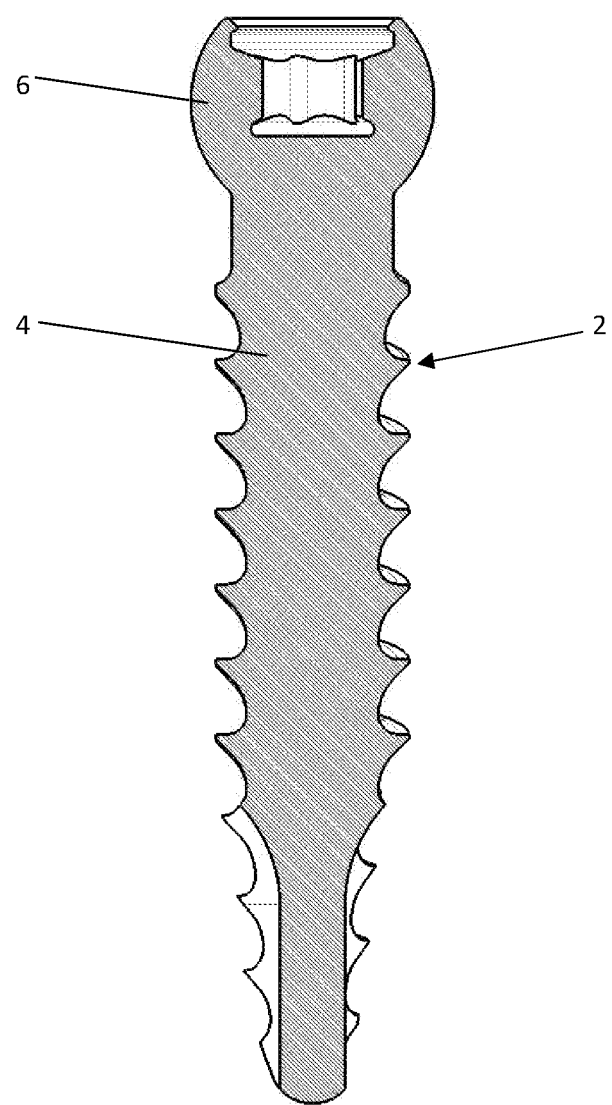

FIG. 11 shows the tool 100 being removed from the tulip assembly 10.

Figure 12:
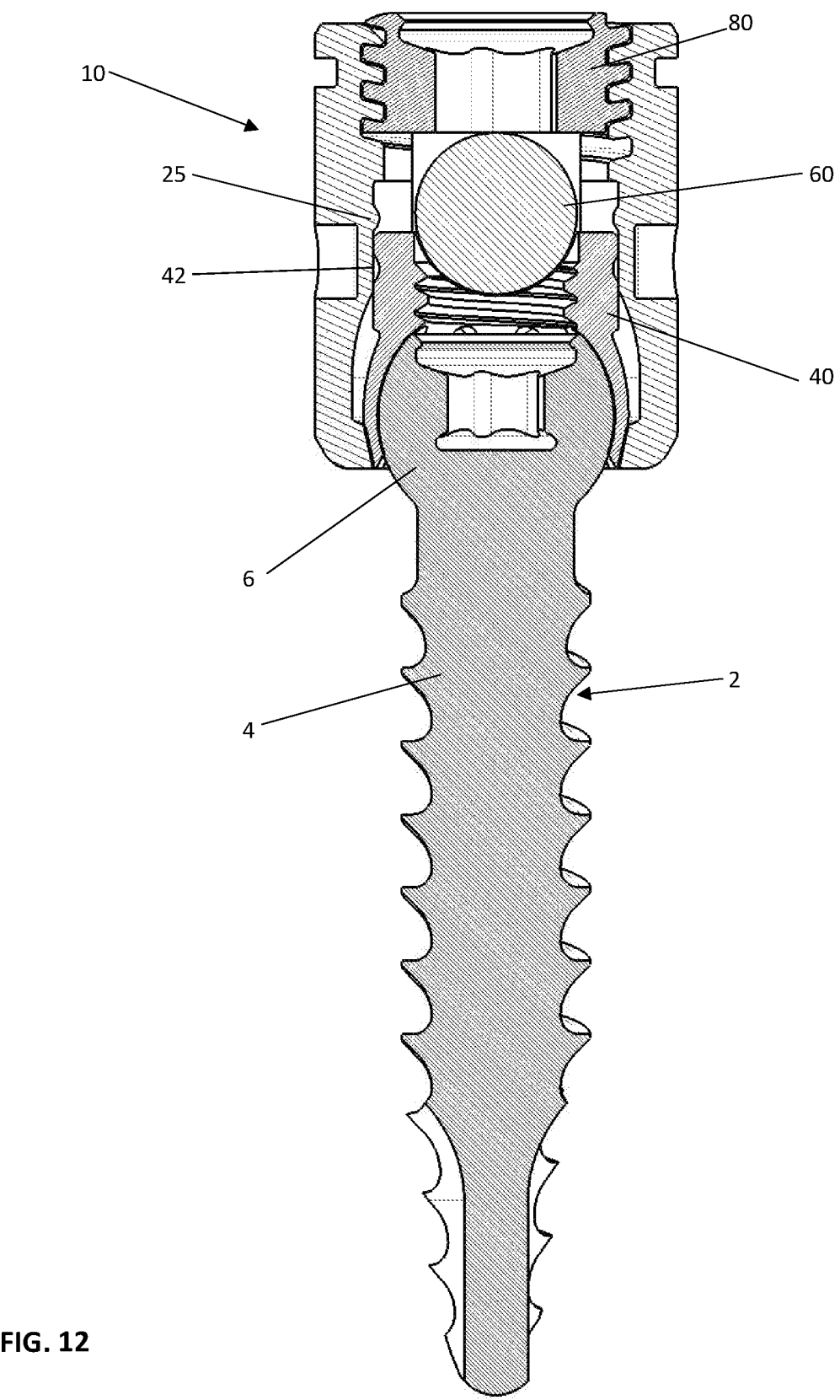
FIG. 12 is a cross-sectional view showing the tulip assembly wherein the internal saddle has been moved to the locked position or state and an exemplary fixation rod is being held in the proximal end of the saddle securely fixed by the exemplary set screw threadingly engaged in the internal threads of the two opposing walls of the tulip.

With reference to FIG. 12, once the assembly is made, it is possible to place a spinal fixation rod 60 into the concavity at the proximal end 44 of the saddle 40. Once the rod 60 is in position, a threaded set screw 80 can be driven down into the internal threads 24 of the opposing walls 22, 23 of the tulip 20. The set screw 80 will then lock the rod 60 into position. When this occurs, the entire assembly is locked into a locked position.

While the embodiment shown shows a single projection 25 is used for the locked position, and a movement of the saddle 40 from an unlocked initial state with the recess or groove 42 on the projection 25 to a locked position when in use, it is understood that a resistance or force required to move the saddle 40 into the preloaded unlocked position for assembly can be adjusted depending on the amount of interference that is provided between the projection 25 and the groove or recess 42 and the exterior surface of the proximal end 44 of the saddle 40. It is believed to have sufficient locking strength, it is preferable that the exemplary tool 100 be used so that the forces required to overcome the initial unlocked state where the recess 42 is positioned over the projection 25 are such that a tool 100 is preferred. The tool 100 designed provides a force between the tulip 20 and the saddle 40, but provides not lifting or pulling forces against the bone screw 2 which can be embedded in bone. This is important in that one does not want to loosen a bone screw 2 that has been attached into a vertebral body, but rather would like the forces for locking the saddle 40 in positon relative to the tulip 20 be absorbed between the tool 100, the tulip 20 and the saddle 40 without any particular axially loads pulling or loosening the bone screw 2.

These and other objectives are achieved by the application of the present invention as described above.

To load the saddle 40 in the tulip 20, a tool is required. A load of 50 to 250 pounds force is believed to be an acceptable range to move the saddle 40 in the preloaded unlocked position with the groove 42 moved onto the projection 25, preferably this load averages 100 pounds. The load to move to the locked position has the same range of 50 to 250 pounds, preferably 100 pounds. As these loads are relatively high, the tool is needed. Interestingly, the saddle 40, when unlocked and ready to receive a pedicle screw head 6, has the plurality of fingers 52 configured to easily deflect allowing a surgeon to place the modular tulip assembly 10 onto the head 6 of an implanted bone screw 2 with very little force, 2.0 to 20.015, typically 5 pounds or less. This low positioning force allows the surgeon to feel the fingers 52 slide over the screw head 6 past the maximum diameter while the force drops and the fingers 52 slide and move back to an undeflected or less deflected state. The fingers 52, once over the screw head, hold the modular tulip assembly in place until the surgeon uses the tool to move the saddle to the locked position. Thereafter, a rod 60 and set screw 80 can be affixed to complete the fixation. The pedicle screw 2 of the present invention has a major thread diameter of 4.0 mm to 10.5 mm and a length of 25 mm to 110 mm. While the locking features of the modular tulip assembly are shown with a tulip 20 and saddle 40 configured to receive a pedicle screw 2, it is understood the locking connector or other assemblies and is not limited to a single rod receiving tulip body.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of assembling a tulip assembly comprising the steps of:
   providing a tulip with a locking projection;
   positioning a saddle with a concave locking surface onto the locking projection in an unlocked state to receive a head of a bone screw;
   placing the tulip with saddle onto the head of the bone screw threaded into bone; and
   moving the saddle to a locked state by moving the concave locking surface past the locking projection by engaging internal threads of the saddle with a threaded end of a tool and rotating the tool to axially move the saddle from the unlocked state to the locked state on the head of the bone screw.

2. The method of assembling a tulip assembly of claim 1 further comprising the step of:
   moving the saddle from the locked state to the unlocked state by engaging internal threads of the saddle with the threaded end of the tool and rotating the tool to axially move the saddle proximally relative to the tulip.

3. The method of assembling a tulip assembly of claim 2, wherein the tool provides a force between the tulip and the saddle, without pulling or loosening the bone screw.

4. The method of assembling a tulip assembly of claim 2, wherein the tool abuts a proximal end of the tulip.

5. The method of assembling a tulip assembly of claim 2, wherein an outer shoulder of the tool abuts a proximal end of the tulip.

6. The method of assembling a tulip assembly of claim 2, wherein the tool provides a force between the tulip and the saddle, without providing lifting or pulling forces against the bone screw threaded into bone.

7. The method of assembling a tulip assembly of claim 1 further comprising the step of:
   moving the saddle from the locked state to the unlocked state by rotating the tool.

8. A method of assembling a tulip assembly comprising the steps of:
   providing a tulip with a locking projection;
   positioning a saddle inside the tulip, wherein the saddle has a locking groove or recess;
   affixing the locking groove or recess to the locking projection to position the saddle in an unlocked state to receive a head of a bone screw;
   placing the tulip with saddle onto the head of the bone screw threaded into bone; and
   moving the saddle to a locked state on the head of the bone screw by moving the locking groove or recess past the locking projection by engaging internal threads of the saddle with a threaded end of a tool and rotating the tool to axially move the saddle from the unlocked state to the locked state on the head of the bone screw.

9. A method of assembling a tulip assembly of claim 8 further comprising the step of:
   moving the saddle from the locked state to the unlocked state by rotating the tool.

10. A method of assembling a tulip assembly of claim 9, wherein the tool abuts a proximal end of the tulip.

11. A method of assembling a tulip assembly of claim 9, wherein an outer shoulder of the tool abuts a proximal end of the tulip.

12. A method of assembling a tulip assembly of claim 9, wherein the tool provides a force between the tulip and the saddle, without providing lifting or pulling forces against the bone screw threaded into bone.

13. The method of assembling a tulip assembly of claim 9, wherein the tool provides a force between the tulip and the saddle, without pulling or loosening the bone screw.

14. A method of assembling a tulip assembly comprising the steps of:
- providing a tulip with a locking projection;
- positioning a saddle inside the tulip, wherein the saddle has a locking groove or recess;
- affixing the locking groove or recess to the locking projection to position the saddle in an unlocked state to receive a head of a bone screw;
- placing the tulip with saddle onto the head of the bone screw threaded into bone;
- engaging internal threads of the saddle with a threaded end of a tool; and
- moving the saddle to a locked state on the head of the bone screw by moving the locking groove or recess past the locking projection by rotating the tool.

15. A method of assembling a tulip assembly of claim 14 further comprising the step of:
- moving the saddle from the locked state to the unlocked state by rotating the tool.

16. A method of assembling a tulip assembly of claim 15, wherein the tool abuts a proximal end of the tulip.

17. A method of assembling a tulip assembly of claim 15, wherein an outer shoulder of the tool abuts a proximal end of the tulip.

18. A method of assembling a tulip assembly of claim 15, wherein the tool provides a force between the tulip and the saddle, without providing lifting or pulling forces against the bone screw threaded into bone.

19. The method of assembling a tulip assembly of claim 15, wherein the tool provides a force between the tulip and the saddle, without pulling or loosening the bone screw.

* * * * *